United States Patent
Gallant

(10) Patent No.: US 10,058,447 B2
(45) Date of Patent: Aug. 28, 2018

(54) LUBRICATING CONDOM

(71) Applicant: Esther Gallant, Newport Beach, CA (US)

(72) Inventor: Esther Gallant, Newport Beach, CA (US)

(*) Notice: Subject to any disclaimer, the term of this patent is extended or adjusted under 35 U.S.C. 154(b) by 221 days.

(21) Appl. No.: 14/108,115

(22) Filed: Dec. 16, 2013

(65) Prior Publication Data

US 2015/0164683 A1    Jun. 18, 2015

(51) Int. Cl.
*A61F 6/04* (2006.01)
*A61F 6/00* (2006.01)

(52) U.S. Cl.
CPC .............. *A61F 6/04* (2013.01); *A61F 6/005* (2013.01); *A61F 2006/049* (2013.01)

(58) Field of Classification Search
CPC .... A61F 6/04; A61F 6/005; A61F 6/02; A61F 2006/048; A61F 2006/043; A61F 2006/047; A61F 5/41
See application file for complete search history.

(56) References Cited

U.S. PATENT DOCUMENTS

| | | | |
|---|---|---|---|
| 2,410,460 A * | 11/1946 | Robinson | A61M 31/00 128/844 |
| 5,284,158 A * | 2/1994 | Mallette | A61F 6/04 128/844 |
| 5,542,914 A | 8/1996 | Van Iten | |
| 2004/0078013 A1 | 4/2004 | Zunker et al. | |
| 2006/0173405 A1 | 8/2006 | Haithcock | |
| 2007/0032758 A1 | 2/2007 | Chase et al. | |
| 2007/0060998 A1 | 3/2007 | Butterwick et al. | |
| 2009/0155354 A1 | 6/2009 | McLean | |
| 2010/0126513 A1 | 5/2010 | Hui | |
| 2010/0204542 A1* | 8/2010 | Hodge | 600/39 |
| 2011/0067707 A1* | 3/2011 | Hui | 128/844 |
| 2011/0073117 A1 | 3/2011 | Hui | |
| 2012/0031409 A1 | 2/2012 | Blum et al. | |
| 2012/0048752 A1 | 3/2012 | Madigan et al. | |
| 2012/0073579 A1* | 3/2012 | Levy | A61F 6/04 128/844 |
| 2013/0146614 A1 | 6/2013 | Madigan | |

FOREIGN PATENT DOCUMENTS

DE  19922537 A1  11/2000
GB  2417231 A  2/2006

OTHER PUBLICATIONS

International Search Report dated Mar. 17, 2015, ISA/US.

* cited by examiner

*Primary Examiner* — Kari Rodriquez
(74) *Attorney, Agent, or Firm* — Fulwider Patton LLP

(57) ABSTRACT

A condom that includes a lubrication packet affixed thereto, the lubrication packet occupying a space that coincides with a fluid receptacle. The packet is filled with lubricant and the integrity of the packet is breached prior to intercourse, releasing the lubricant inside the body lumen over a period of time. Once the packet is substantially depleted, a void created by the depleted packet can be used by the receptacle.

1 Claim, 1 Drawing Sheet

LUBRICATING CONDOM

BACKGROUND

Sexual intercourse is a rewarding part of a healthy and active adult life. In the case of vaginal intercourse, the female physiology is particularly suited to facilitate the act through various changes that take place in the female reproductive system, including lengthening of the vaginal canal, contraction of the muscles surrounding the vagina, and secretions of several glands at the back of the vagina, secretions (sweating) directly from the interior vaginal wall, and secretion of the Bartholins glands at the entrance of the vagina, which secrete relatively minute amounts of fluid (one or two droplets of fluid when the female is sexually aroused). These minute droplets of fluid for lubrication were once believed to be important for lubricating the vagina, but research from Masters and Johnson demonstrated that vaginal lubrication comes primarily from deep within the vagina. The (Bartholins gland) fluid may slightly moisten the labial opening of the vagina, serving to make contact with this sensitive area more comfortable for the woman. Given the vast array of commercially available lubricants for external application, it is clear that for a variety of reasons, some herein discussed, the naturally secreted minor lubrication from the labial opening, is insufficient in many cases, to provide adequate lubrication, with the vast majority of secretions coming from deep within the vagina. All of these changes take place in a healthy female and promote a pleasurable experience for each participant.

While these changes in a woman's body occur during intercourse, many women complain about insufficient secretions causing vaginal discomfort and irritation during or after intercourse. In addition to the absence of the frequent vulvo-vaginal inflammatory-infectious conditions, and of the dryness and hypotrophy of these organs resulting from the post-menopausal estrogen fall, one of the causes for this vaginal irritation during and after intercourse, is vaginal penetration before women are adequately aroused. Considering that the first reaction of the female genitals to sexual excitement is vaginal lubrication, if a woman is penetrated without being properly aroused and, therefore, without the occurrence of the necessary physiological vaginal lubrication, several symptoms of vulvo-vaginal discomfort may occur. In addition, even when adequately aroused, many women suffer from insufficient lubrication for a variety of reasons, some of which have already been mentioned. Insufficient lubrication may also cause a degree of discomfort and irritation to the male penis.

Transudation is the process resulting in vaginal lubrication. When a female is sexually aroused, blood flows into the area surrounding the walls of the vagina in a process called vasocongestion. The pressure of the increased blood causes a seepage of moisture from the spaces between the cells. This moisture cresses the vaginal lining, first appearing as tiny droplets. Eventually, the fluid builds up in sufficient quantity to moisten the entire inner walls of the vagina. In the excitement phase, blood flow to the vagina increases which, in turn, pushes fluid into the vaginal canal. This lubricating process allows for comfortable penile insertion, and repetitive insertions during intercourse.

Natural cyclic hormonal alterations, stress, and the use of combined or progestin-only hormonal contraceptives, if applicable, affect the amount and the consistency of vaginal lubrication during normal daily activities and during sexual arousal. Many medications that women use to treat other conditions can adversely affect vaginal lubrication. These medications include antihistamines, anticholinergics, antihypertensives, and most psychoactive agents, particularly SSRIs and benzodiazepines. Women of any age have various reasons for augmenting their natural vaginal secretions with lubricants or moisturizers to facilitate comfort before, during, and after sexual activity. Additionally, repetitive penetration during intercourse may cause the drying out of the lubrication prior to the completion of the activity. Many men, as well as women, also prefer additional lubrication during sexual activity to increase both their and their partner's enjoyment of sexuality.

One problem with traditional methods and products for augmenting the body's natural lubrication system is that the lubricant is applied at the entrance to the vaginal (or anal) opening. This is unsatisfactory for several reasons. The female body's natural lubrication system secretes lubricant from deep inside the body lumen, where the act of intercourse spreads the lubricant along the walls of the vagina. If the lubricant is applied either to the penis or the entrance of the vagina, the large majority of the lubricant is sheared, and wiped off by the penetrating motion of the penis, greatly diminishing the lubricant's usefulness. Existing commercial products to augment a woman's natural lubrication system are applied, at or close to the vaginal opening, and cannot reproduce the body's design to lubricate from well within the body lumen. The present invention is intended to overcome this shortcoming.

A condom is a sheath that is closed on one end and worn over the penis during sexual intercourse. When used properly latex condoms can lower the risk of spreading many sexually transmitted diseases. More importantly, condoms do not have the serious side effects for their users that are sometimes associated with other birth control methods. Condoms generally come pre-lubricated but some condoms are lubricated more than others. Condoms without lubrication are also available. However, oil-based lubricants should never be used with latex and polyisoprene condoms because oil may weaken the condom material. While lubricated condoms are well known in the art, they suffer the same issue as discussed above, in that the lubrication can be driven off at the entrance of the body cavity by the tissue surrounding the entrance of the body cavity. The present invention seeks to overcome this shortcoming.

SUMMARY OF THE INVENTION

The present invention is a lubricating condom that includes a parabolic, or U-shaped packet of lubrication affixed to the tip of the condom. When the condom is placed on the penis, the U-shaped packet of lubricant is preferably over the glans at the leading edge, where it can enter the cavity prior to the rest of the condom. Prior to intercourse, the packet can be pierced, pricked, or otherwise unsealed, slowly releasing lubrication from the tip of the condom at the back of, and all along, the body lumen. During intercourse, by the action of intercourse, pressure on the packet releases lubricant slowly and continuously inside the body cavity, where it is spread over the lumen walls by the condom. Because the lubricant is released inside the body cavity, the problem of the lubrication being wiped away during penetration and intercourse is obviated. In this manner, lubrication is released within the body cavity in a manner similar to the body's own lubrication system. The shape of the packet allows the condom's customary reservoir tip to sit in a void in the packet. As the pouch is depleted of the lubricating material, the intended space for the reservoir tip of the condom is made available for its intended purpose.

It should be noted that while the present invention is described herein with respect to the application of lubricant, it is to be understood that the present invention has other uses as well, including delivery of medicinal products, vitamins, nutrients, and other materials that from time to time need to be inserted into a body lumen. Accordingly, the invention is intended to encompass all such applications and uses, and is not to be limited to those described herein.

BRIEF DESCRIPTION OF THE DRAWINGS

The invention is described below in the detailed description of the preferred embodiments, which reference the following drawings accompanying this application.

DETAILED DESCRIPTION OF THE PREFERRED EMBODIMENTS

Figure 1:
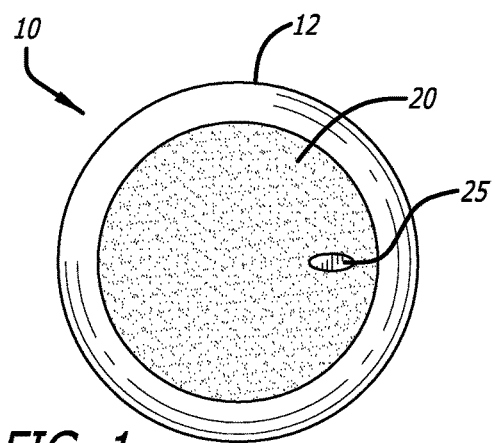
FIG. 1 an elevated, perspective view of a condom and packet combination of the present invention in the rolled up state.
Figure 2:
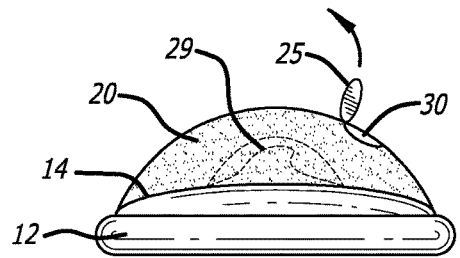
FIG. 2 is a top view of the embodiment of FIG. 1.
Figure 3:
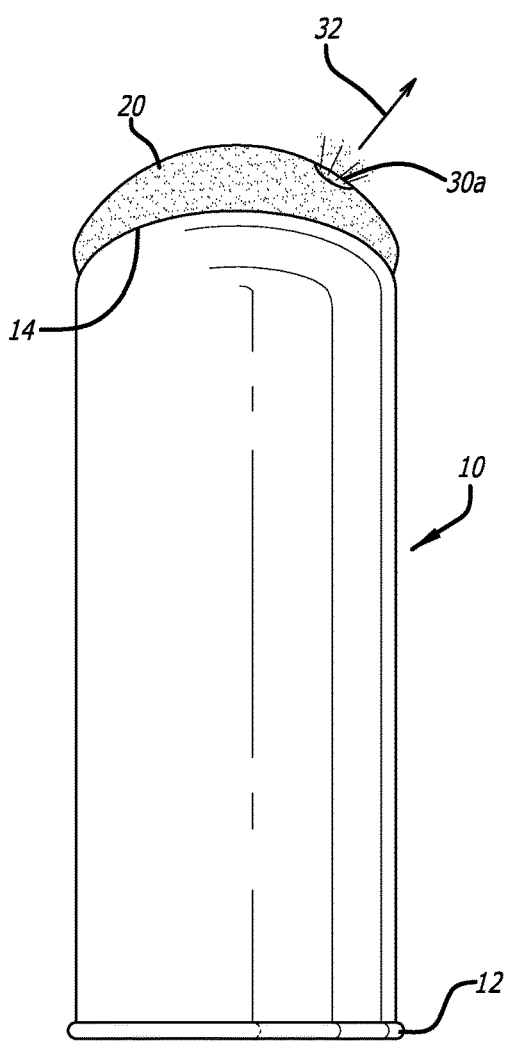
FIG. 3 an enlarged, elevated perspective view of the condom while deployed.

FIGS. 1 through 3 illustrate a first preferred embodiment of the present invention characterized by a condom 10 that is similar to various condoms that are sold in the market today, and who's description and composition are well known in the art. The condom 10 is shown in the "rolled-up" condition looking down from above in FIG. 1. In the compact or rolled-up condition, the material that forms the body of the condom is collected in a circumferential ring 12, leaving an exposed top portion 14. As can be seen in FIG. 2, a reservoir tip 29 is located on the distal end of the condom 10. In the condom 10 of the present invention, a separate, self-contained, U-shaped packet 20 is affixed to the top portion 14 of the condom 10. The U-shaped packet 20 may be affixed by a biocompatible adhesive, heat melt, or other suitable mechanical attachment method, or pre manufactured as a multi-part 'to be assembled' condom set, or as a single compartmentalized condom, that will ensure that the packet 20 will remain affixed to the condom 10 throughout the act. The packet 20 may be sold separately from the condom 10 to be attached to the users condom of choice, or it may be sold as a condom with packet, multi-part set, or as pre manufactured compartmentalized single condom units. Manufacturing issues of latex condoms may make it more desirable to have a two-piece arrangement that are assembled prior to use, where the packet 20 is placed over the condom 10 with a quick acting biocompatible adhesive just prior to intercourse.

Although the packet can take various shapes, the preferred shape is a U-shaped configuration that includes a semi-spherical upper surface and has an underside that includes a void to accommodate the condom's reservoir tip. The lubricant containing packet can be prepared to release the contained fluid in various ways, although the most efficient is simply pricking the upper surface with a needle or pin 32. Other means for releasing the lubricant include a small tab 25 that seals the upper surface of the packet 20. The tab 25 can be pulled back prior to penetration, revealing a small hole 30 that allows lubricant inside the packet 20 to slowly leak out as the penis penetrates the body lumen. The hole 30 formed when the tab 25 is pulled back is correctly sized, so that the lubricant will be emitted slowly and continuously over the course of the act of intercourse, providing continuing lubrication during the act. Further, the lubrication will be dispensed inside the body cavity as opposed to outside the cavity, where it can be sheared off during penetration. In this manner, the condom 10 of the present invention lubricates the body lumen in a manner similar to the body's own lubrication system. Additionally, when the packet is pierced, a tiny amount of lubricant can begin to leak out providing lubricant at the entrance of the body lumen upon penetration, and continue to release lubricant well within the body lumen, as described.

An ordinary pin 32 (see FIG. 3) or a pin type object can be enclosed with the product, and can be used to prick the packet 20 to create a small seepage hole 30a through which the lubricant can leak out, or the packet 20 can have one or more small pin holes that are covered by a small piece of tape or removable cover (not shown). The packet 20 may be sold as a separate item that is placed on the condom of the user's choice, either before unfurling the condom or after the condom is placed on the penis. In this example, the packet 20 will include a multipurpose adhesive that can reliably affix to latex, lubricated, non-lubricated, natural materials such as sheep skin or the like. The adhesive should be safe and bio-compatible so as not to cause irritation or damage to the involved tissues. A vegetable gum might be an example of a safe biocompatible adhesive. Moreover, the packet 20 can be filled with various lubricants that are known in the art.

Figure 4:
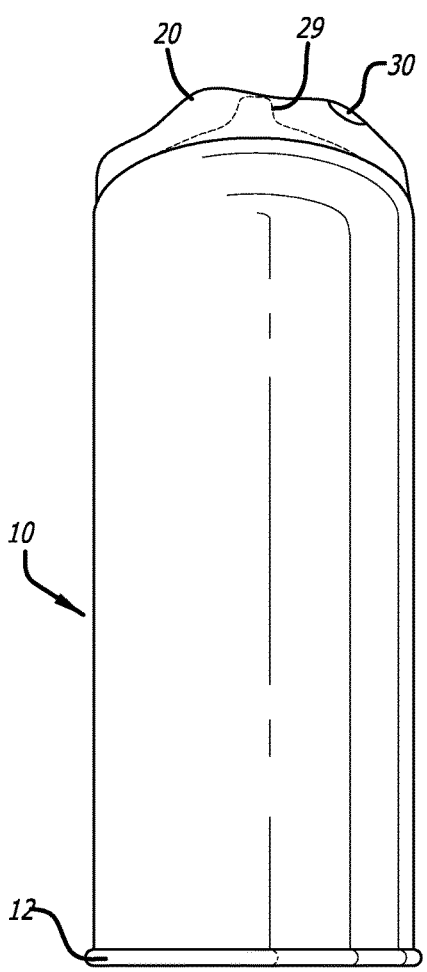
FIG. 4 is an elevated perspective view of the embodiment of FIG. 3 after the packet is depleted.

As shown in FIG. 4, the packet 20 creates a void as it emits the lubricant until the packet 20 is depleted. Typically condoms include a reservoir tip 29 to collect semen that is ejaculated. The condom's reservoir tip in the present invention can thus replace the void created by the empty packet once the lubricant is expelled therefrom. This exchange allows the condom 10 of the present invention to create virtually no more space than existing condoms while adding a unique and beneficial lubrication function. In this manner, the condom of the present invention is an advance in the art.

The embodiments just described and depicted in the accompanying drawings are not intended to be limited, but rather exemplary of the modes and uses of the present invention. It is to be understood that various modifications and alternate uses are envisioned, and the present invention is intended to encompass all such modifications and alternate uses as would be understood by one of ordinary skill in the art.

I claim:
1. A condom, comprising:
a body portion rolled into a circumferential ring and a top portion disposed within the circumferential ring, the top portion including a reservoir tip comprising an elongate tubular extension that extends from above the top portion; and
a lubrication packet having a semi-spherical upper surface and a lower surface and a quantity of lubricant disposed therebetween, the lower surface of the lubrication packet separate from the top portion, the lower surface having a first portion connected to the top portion of the body portion and a central void detached from the top portion to establish a void over the elongate tubular extension of the reservoir tip where a gap is formed between the lubrication packet and the elongate tubular extension of the reservoir tip, the lubrication packet extending to the circumferential ring, and the lubrica- tion packet having a dedicated opening for emitting lubrication from the packet through the opening;

a tab on the lubrication packet for covering the opening, where said tab is configured to be manually deployed to uncover the opening and release the lubricant; and wherein the elongate tubular extension of the reservoir tip when filled with semen expands longitudinally so as is adapted to extend through the central void of the lower surface of the lubrication packet into the lubrication packet once the lubrication packet is depleted of its contents.

\* \* \* \* \*